United States Patent [19]

Dittrich et al.

[11] Patent Number: 5,919,883
[45] Date of Patent: Jul. 6, 1999

[54] PROCESS FOR PREPARING POLYORGANOSILOXANES WHICH COMPRISE SUBSTANTIALLY NO CYCLIC COMPONENTS AND USE OF THE PROCESS TO PREPARE ORGANOFUNCTIONALLY MODIFIED POLYSILOXANES

[75] Inventors: Uwe Dittrich, Radebeul; Holger Rautschek, Nuenchritz; Harald Schickmann, MeiBen, all of Germany

[73] Assignee: Huels Silicone GmbH, Nuenchritz, Germany

[21] Appl. No.: 08/849,219

[22] PCT Filed: Dec. 6, 1995

[86] PCT No.: PCT/EP95/04793

§ 371 Date: Aug. 15, 1997

§ 102(e) Date: Aug. 15, 1997

[87] PCT Pub. No.: WO96/18670

PCT Pub. Date: Jun. 20, 1996

[30] Foreign Application Priority Data

Dec. 12, 1994 [DE] Germany .............. 44 44 173
Dec. 12, 1994 [DE] Germany .............. 44 44 174

[51] Int. Cl.$^6$ .................................. C08G 77/06
[52] U.S. Cl. ................. 528/15; 528/23; 528/16; 528/18
[58] Field of Search ............... 528/23, 15, 16, 528/18

[56] References Cited

U.S. PATENT DOCUMENTS 3,715,334  2/1973  Karstedt ........................... 528/15
5,110,969  5/1992  Dittrich et al. .
5,270,424  12/1993  Drake .............................. 528/15
5,540,221  5/1995  Razzano .......................... 528/16

FOREIGN PATENT DOCUMENTS 0 195 936  10/1986  European Pat. Off. .
0 251 435  1/1988  European Pat. Off. .
35 33 028  3/1987  Germany .

OTHER PUBLICATIONS

Chemical Abstracts, vol. 116, AN–84454a, JP 3–221 530, Sep. 30, 1991.
Derwent Abstracts, AN 74–34821V/19, FR 2 203 821, Jul. 21, 1974.
Derwent Abstracts, AN 82–06448E/04, GB 2 079764, Jan 27, 1982.

Primary Examiner—Melvyn I. Marquis
Assistant Examiner—Mark W. Milstead
Attorney, Agent, or Firm—Oblon, Spivak, McClelland, Maier & Neustadt, P.C.

[57] ABSTRACT

The invention relates to a process for preparing polyorganosiloxanes which comprise substantially no cyclic components and have uniform molecular weight distribution by reacting organosilicon compounds which have no condensable groups in the presence of a catalyst which exclusively promotes equilibration and suppresses formation of cyclic components. The resulting polyorganosiloxanes have a linear or branched structure. They can either be used immediately, for example in silicone rubbers and silicone greases, as components in release agents, in impregnating agents, in antifoams, etc., or are starting compounds for preparing organofunctionally modified polysiloxanes which are obtained by hydrosilylation of the polyorganosiloxanes with hydrocarbons and/or organic polymers.

15 Claims, 1 Drawing Sheet

PROCESS FOR PREPARING POLYORGANOSILOXANES WHICH COMPRISE SUBSTANTIALLY NO CYCLIC COMPONENTS AND USE OF THE PROCESS TO PREPARE ORGANOFUNCTIONALLY MODIFIED POLYSILOXANES

TECHNICAL FIELD

The invention relates to a process for preparing polyorganosiloxanes which comprise substantially no cyclic components and have process molcular weight distribution by reacting organosilicon compounds which have no condensable groups in the presence of a catalyst which exclusively promotes equilibration and suppresses formation of cyclic components. The resulting polyorganosiloxanes have a linear or branched structure. They can either be used immediately, for example in silicone rubbers and silicone greases, as components in release agents, in impregnating agents, in antifoams, etc., or are starting compounds for preparing organofunctionally modified polysiloxanes which are obtained by hydrosilylation of the polyorganosiloxanes with hydrocarbons and/or organic polymers.

PRIOR ART

A common process for preparing polyorganosioxanes is the ring-opening polymerization of oligomeric cyclic siloxanes. This process can be accelerated by means, for example, of basic catalysts. Examples thereof are tetramethylammonium hydroxides (EP 492 662; Spinu, M. et al.: J. Polym. Sci. A, Polym. Chem. 29 657 (1991)), cesium hydroxides (DE 26 19 187) or sodium or potassium hydroxide (U.S. Pat. No. 4,122,247; Fish, D. et al.: Makromol. Chem. Macromol. Symp. 32 241 (1990)) and also the siloxanolates and silanolates derived from these hydroxides. In this process, from 10 to 15% by weight of the cyclic starting materials remain in the end product as a result of the thermodynamic equilibrium which is established. To prepare pure polyorganosiloxanes, therefore, a laborious vacuum distillation is required which, especially in the case of highly viscous products, gives rise to considerable technical problems.

When acidic catalysts are used for the ring-opening polymerization, equilibrium cyclic compounds again remain in the product. Examples of customary acidic catalysts are acidic ion exchangers and acid-activated bleaching earths (U.S. Pat. No. 4,831,174), trifluoromethanesulfonic acid (Penczek, S. et al.: Adv. Polym. Sci. 68/69 216 (1986)), and phenyldimethylsilyl perchlorate (U.S. Pat. No. 5,196,559). Even if the polymerization is initiated by an entirely different mechanism, by means of gamma rays (Sigwalt, P. et al.: Makromol. Chem. Macromol. Symp. 32 217 (1990)), because of the cyclic compounds which remain it is impossible to do without a distillation step.

The position of this equilibrium is independent of the catalyst used (Kendrick, T. C. et al. in "The Chemistry of Organosilicon Compounds" ed. by S. Patai and Z. Rappaport, J. Wiley & Sons Ltd 1989, p.1289), of the concentration of catalyst and also of the temperature (Penczek, S. et al.: Adv. Polym. Sci. 68/69 216 (1986)).

Equilibrium cyclic compounds can be regarded as unavoidable, and their formation is known to the skilled worker (Demby, D. H.: Chem. Ind. (Dekker) 1993 43 183). The underlying scientific laws have been investigated both theoretically by the Nmobel prizewinner P. Flory (J. Am. Chem. Soc. 88 3209 (966)) and practically (Brown, J. F. et al. ibid 87 931 (1965)).

Where the intention is to prepare polyorganosiloxanes containing no volatile by-products or unreacted starting materials, then the reaction must be carried out such that the thermodynamic equilibrium is not reached but instead the product composition is controlled kinetically.

It is known that the polycondensation of hydroxy-terminated polyorganosiloxanes can be carried out with kinetic control. Typical catalysts for this reaction are alkylsulfonic acids (EP 314 315), trifluoromethanesulfonic acid (U.S. Pat. No. 4,696,970), alkali metal borates (EP 382 367) and phosphorus nitride halides (DE 12 62 020, DE 22 29 514). These processes require the presence of condensable groups and the removal of volatile by-products of the condensation (e.g. water). However, if the process regime is inappropriate (excessive duration of action of the catalyst), here again there is the risk of the formation of cyclic oligomeric siloxanes (DE 12 62 020).

The polymerization of cyclotrisiloxanes, which because of the ring strain is highly exothermic, can also be controlled kinetically when initiated with basic lithium compounds. If the polymerization is terminated at the appropriate time, before the equilibrium is established, it is possible to obtain polyorganosiloxanes whose content of cyclic siloxanes is so low that a distillation step is no longer necessary (EP 455 163, JP 02 289 623). In this case, the choice of starting materials is restricted: for example, a basic catalyst does not permit preparation of polymers containing silicon-bonded hydrogen. Moreover, the process regime demands particularly close attention to determine at what point to terminate the reaction.

Since these known, kinetically controlled processes are polycondensation or addition polymerization reactions where any equilibration is suppressed, it is not possible to achieve a uniform molecular weight distribution and a uniform, statistically controlled distribution of terminal or lateral functional groups, especially if the starting materials comprise siloxanes having different terminal and/or lateral functional groups or different molecular weights. With the processes and catalysts known to date, organosiloxanes of uniform composition are only obtained if the equilibrium has been reached, and thus also if the equilibrium cyclic compounds which remain or which form in accordance with the laws are present. This means that in many cases an additional, cost-intensive distillation step is necessary in order to remove the cyclic compounds. The thermal stress associated with this can cause difficulties for the product, for example if silicon-bonded hydrogen atoms or vinyl groups should be present in the polymer, which are unable to withstand high thermal stress.

Siloxanes of uniform composition are required for numerous applications, for example if Si—H groups are to be incorporated into polyorganosiloxanes which are reacted to form specific polyorganosiloxanes, for example polyether-functional polyorganosilixoanes, or if a statistically controlled distribution of trimethylsiloxy and dimethylvinylsiloxy end groups is required for the synthesis of specific polymers.

The synthesis of organofunctionally modified polysiloxanes is—as is known—an at least two-stage process. In this process the preparation of a siloxane containing Si—H bonds in the first step, is followed by the functionalization of this siloxane with a very diverse range of organic radicals, commonly by hydrosilylation with the corresponding unsaturated, functional or nonfunctional, organic compounds, customarily in the presence of platinum or rhodium compounds as catalyst. This fundamental synthesis route and the modified polysiloxanes obtainable thereby have been described on numerous occasions (e.g. J. W. Adams in "Surf. Phenom. and Additives in Water-Based Coatings and Printing Technology", Plenum Press New York 1991, 73–82).

The step which is critical for the structure and thus, ultimately, for the effectiveness of the organofunctionally modified polysiloxanes in the very diverse range of applications is the synthesis of the hydrido-functional polysiloxane in the 1st stage. Where—in accordance with the prior art—cyclic siloxanes remain in the product, they reduce its effectiveness or must be removed by means of laborious vacuum distillations. Owing to small amounts of remaining catalysts and thus a virtually unobtainable ideal pH of 7 these distillations are accompanied by side reactions, with elimination of $H_2$ and formation of unwanted silanol groups, which ultimately by way of side reactions adversely affect the properties, the behavior and the effectiveness of the organofunctionally modified polysiloxanes prepared in the subsequent reaction. Irrespective of this, the distillation of, for example, highly viscous hydrido-functional polysiloxanes is extremely problematic.

It was therefore highly desirable to develop a process which permits the preparation of polyorganosiloxanes with a uniform molecular weight distribution by equilibration in one step and with substantially no cyclic components being formed.

DESCRIPTION OF THE INVENTION

The invention provides a process for preparing polyorganosiloxanes which comprise substantially no cyclic components and have a monomodal molecular weight distribution and a statistical distribution of the functional groups present by means of equilibration.

The invention also provides for the preparation of organofunctionally modified polysiloxanes, where the hydrido-functional polyorganosiloxanes prepared in a first stage by equilibration, which comprise substantially no cyclic components, are reacted with hydrocarbons and/or organic polymers in the presence of a hydrosilylation catalyst.

In accordance with the invention, two or more organosiloxanes and/or polyorganosiloxanes of the general formula $$R_aSiO_{(4-a)/2} \quad (I),$$

which comprises at least one siloxy group of the general formula $$R_3SiO_{0.5}- \quad (M),$$

and comprises at least one siloxy group of the general formula $$-R_2SiO- \quad (D),$$

in which R denotes identical or different, saturated and/or unsaturated, substituted and/or unsubstituted, monovalent hydrocarbon radicals having 1 to 30 carbon atoms or hydrogen, with the proviso that only one hydrogen is attached per silicon, and a denotes integral or fractional numbers greater than 1, preferably from 1.8 to 2.2, which, however, comprise no notable amounts of condensable groups, are reacted in the presence of a catalyst which exclusively promotes equilibration and suppresses formation of cyclic components.

DETAILED DESCRIPTION OF THE INVENTION AND PREFERRED EMBODIMENTS THEREOF

Figure 1:
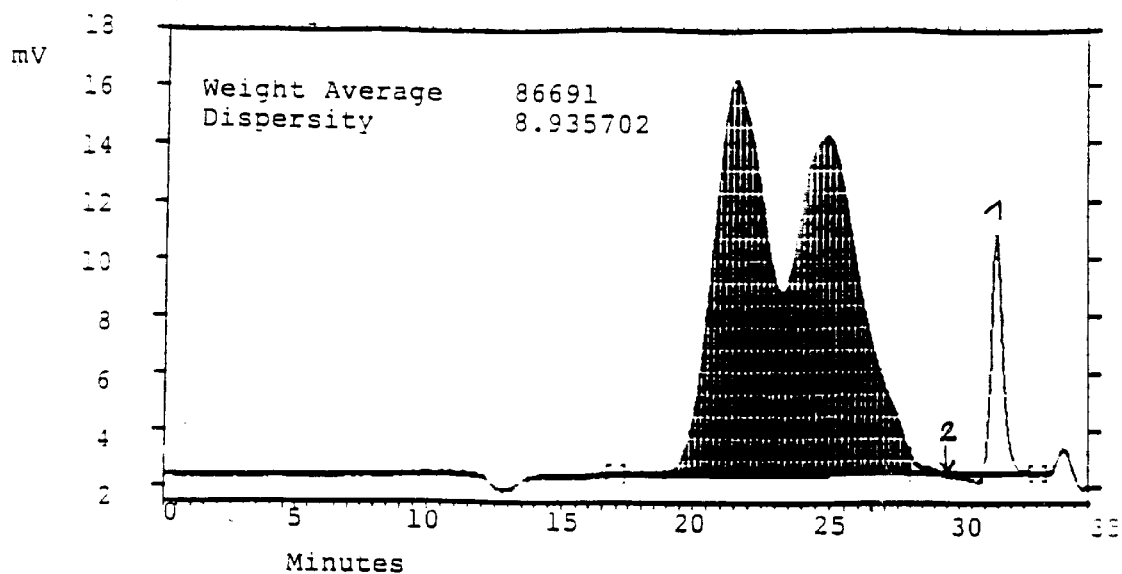
FIGS. 1 and 2 show weight average dispersities of the polyorganosiloxanes obtained by the claimed invention.

As catalysts which exclusively promote the equilibration of linear and/or branched polyorganosiloxanes and which suppress formation of cyclic components it is preferred to employ phosphonitrile chloride or its reaction products.

The phosphonitrile chloride used consists essentially of compounds and/or mixtures of these compounds of the general formula $$[Cl_3PN(PCl_2N)_xPCl_3]^+[P_yCl_{5y+1}]^- \quad (VI)$$

in which x is an integer greater than or equal to 0 and y is 0 or 1. It is obtained, for example, by reacting 2 mol of phosphorus pentachloride with 1 mol of ammonium chloride in accordance with U.S. Pat. No. 3,839,388 and is commonly employed as a solution in methylene chloride.

Compounds which can likewise be employed with good results as catalyst are reaction products of phosphonitrile chloride, for example the reaction product of phosphonitrile chloride with compounds of the general formula $$[R^1_3SiO(R^1_2SiO)_n]_3P=O \quad (II),$$

in which $R^1$ independently at each occurrence denotes identical or different, substituted and/or unsubstituted, unsaturated and/or saturated monovalent hydrocarbon radicals having 1 to 6 carbon atoms or hydrogen, with the proviso that only one hydrogen atom is attached to each silicon atom, and n adopts a value of between 0 and 500, it being possible for volatile, chlorine-containing silicon compounds which form during the reaction to be separated out completely or in part. Phosphonitrile chloride can be reacted in any proportion with the compound of the general formula (II).

It is additionally possible to employ the phosphonitrile chloride in accordance with DE 42 21 854, dissolved in acid chlorides, or to prepare said phosphonitrile chloride by reacting phosphorus pentachloride and ammonium chloride in acid chlorides as solvent. In this context, some or all of the phosphonitrile chloride can also be present as a reaction product with the acid chloride. This does not impair the catalytic activity of the phosphonitrile chloride. Where the preparation is carried out in the presence of phosphorus oxychloride, the partial incorporation of the phosphorus oxychloride additionally gives rise to oxygen-containing by-products which likewise do not reduce the catalytic action, with the consequence that the laborious isolation of the individual phosphonitrile chlorides can be omitted.

As further catalysts which exclusively promote the equilibration of linear and/or branched polyorgano-siloxanes and which suppress formation of cyclic components it is possible to employ compounds of the general formula $$R^2SO_2Y \quad (III),$$

where $R^2$ denotes perfluoroalkyl and/or perfluoroalkylene radicals having 1 to 20 carbon atoms and Y denotes hydroxyl, halogen or $R^2SO_2O$ radicals. For example, the radical $R^2$ in the compound of the general formula (III) can be a perfluoroalkyl and/or perfluoroalkylene radical having 1 to 4 carbon atoms. Preference is given to perfluoroalkylsulfonic acids and their acid halides and/or their acid anhydrides, for example nonafluorobutylsulfonic acid, pentafluoroethylsulfonic anhydride, the mixed anhydride of trifluoromethanesulfonic acid and heptafluoropropylsulfonic acid, trifluoromethanesulfonyl chloride and trifluoromethanesulfonyl fluoride. Particular preference is given to trifluoromethanesulfonic acid, which is relatively easy to obtain.

To implement the novel process it is also possible to adsorb the catalyst on a solid support. The compound of the general formula (III) can also be bound chemically, for example by graft polymerization or copolymerization of a compound in which the radical $R^3$ is unsaturated with perfluorinated olefins or other unsaturated compounds and/or polymers, and can be used, for example, in the form of a polymer membrane.

Further compounds which can be employed as catalysts which exclusively promote equilibration and which suppress formation of cyclic components are silanes and siloxanes containing perfluoroalkylsulfonic ester groups. Such compounds can be prepared, for example, by reacting perfluoroalkylsulfonic acids with cyclic and/or linear siloxanes or by reacting silanols and/or siloxanols with perfluoroalkylsulfonic acids, perfluoroalkylsulfonyl halides and/or perfluorosulfonic anhydrides.

The polyorganosiloxanes employed (general formula (I)) preferably correspond to compounds of the general formula

$$R_3SiO(SiR_2O)_mSiR_3 \qquad (VII)$$

and consist essentially of linear polyorganosiloxanes terminated by monofunctional units. Alternatively, either intentionally or as an impurity, they may comprise trifunctional and tetrafunctional units. The value m in formula (VII) determines the viscosity of the polyorganosiloxanes, which is preferably in the range from 0.65 to 5,000,000 mm$^2$/s, preferably in the range from 10 to 1,000,000 mm$^2$/s.

Examples of the radicals R are n-alkyl radicals having 1 to 20 carbon atoms such as, for example, methyl, ethyl, hexyl and cyclohexyl; isoalkyl radicals having 3 to 20 carbon atoms, such as isopropyl and isoamyl radicals; alkyl radicals with tertiary carbon atoms, such as tert-butyl and tert-pentyl; unsaturated hydrocarbon radicals, such as vinyl, allyl, methacryloyl and hexenyl radicals, aromatic hydrocarbon radicals, for example: phenyl, naphthyl and anthryl radicals; alkylaryl radicals in which the silicon is attached either to an aromatic carbon atom, as, for example, in the case of tolyl radicals, or to an aliphatic carbon atom, as, for example, in the case of benzyl radicals; and also substituted hydrocarbon radicals, for example trifluoropropyl, cyanoethyl, alkoxyaryl, alkoxyalkyl and haloaryl radicals. Particularly preferred radicals R are methyl, phenyl, vinyl and hydrogen radicals.

Examples of compounds of the general formula (I) are, furthermore, polydimethylsiloxanes with trimethylsiloxy end groups, polydimethylsiloxanes with dimethylvinylsiloxy end groups, polydimethylsiloxanes with dimethylhydridosiloxy end groups, polymethylhydridosiloxanes with trimethylsiloxy end groups and/or dimethylhydridosiloxy end groups, polyorganosiloxanes with lateral and/or terminal unsaturated hydrocarbon groups, and also hexamethyldisiloxane and disiloxanes with dimethylvinyl or dimethylhydrido end groups.

The reaction of one or more compounds of the general formula (I) takes place at temperatures in the range up to 250° C., preferably from 10 to 120° C. preferably no water or organic solvents being added.

The reaction times necessary are dependent on the temperature and on the concentration of catalyst and are between 0.5 minutes and 20 hours, usually between 1 minute and 5 hours. The concentration of catalyst can be from 0.1 to 100 ppm by weight, based on the overall weight of the starting materials. The catalyst is preferably employed in concentrations of from 5 to 20 ppm by weight.

Following the reaction, the catalyst is normally deactivated and/or separated off. Separation can be effected, for example, by distillation if the catalyst, for example trifluoromethanesulfonic acid, is volatile. One possibility of deactivation is neutralization using, for example, alkali metal hydroxides, alkali metal silanolates, alkali metal siloxanolates, lithium alkyls, amines, aminosiloxanes, epoxides, vinyl ethers or basic solids such as alkali metal phosphates, alkali metal or alkaline earth metal carbonates or magnesium oxide. If the catalyst is fixed to a support, then simple mechanical separation is a possibility.

Preferably, as compounds of the formula (I), low-viscosity polymers are reacted with polymers of high or higher viscosity to form polyorganosiloxanes having statistically distributed lateral and/or terminal groups and whose mean molecular weight lies between those of the starting materials. An example of this is the preparation of polymers having a statistically controlled distribution of trimethylsiloxy and dimethylvinylsiloxy end groups from trimethylsiloxyterminated polydimethylsiloxanes and dimethylvinylsiloxy-terminated polydimethylsiloxanes. Compounds of this sort can be reacted to form specially branched siloxanes, which can be used, for example, as a constituent of silicone rubbers, silicone gels or antifoams.

The application of the novel process can also be advantageous in cases where specific polymers are to be prepared from standard polymers and where no separate unit with a distillation facility is available. The novel process can be carried out in simple stirred vessels without a vacuum connection and without a distillation receiver with condenser, since the novel process does not give rise to any volatile cyclic siloxanes which must be removed by distillation.

The novel process also of course allows a continuous procedure. If the two components to be equilibrated and the catalyst are passed through a heatable static mixer and then neutralized, likewise in a static mixer, it is possible depending on the nature and quantity of the starting materials to prepare a very diverse range of polymers. Moreover, this process is very easy to control by using, for example, a process viscometer; in other words, at constant viscosity the molecular equilibrium has become established and the reaction is at an end.

Since the polyorganosiloxanes used as starting materials contain no condensable groups, silicon-bonded alkoxy or hydroxyl groups are present only as a technically unavoidable impurity in trace amounts. The reaction of the compounds of the general formula (I) takes place, accordingly, by pure equilibration reactions, with a statistical distribution of terminal and/or lateral functional groups being obtained without the formation of the cyclic siloxanes which, in the view of those skilled in the art, are formed automatically.

The effect of suppressing the formation of cyclic compounds in the course of equilibration, and the search for suitable compounds which catalyze the equilibration of different siloxanes but not the formation of cyclic components, have not been described to date. In all available documents of the prior art, formation of cyclic components is mentioned as a normal secondary phenomenon which has to be accepted in the preparation of siloxanes.

Compounds of the general formula (III) are known, for example, as catalysts for polymerizations of siloxanes, always in conjunction with the formation of equilibrium cyclic compounds.

Phosphonitrile chloride is described in the literature (W. Noll, "Chemie und Technologie der Silicone" Verlag Chemie GmbH, Weinheim/Bergstraße 1968, p.179) as a pure polycondensation catalyst, and its mode of action is restricted to silanol-containing siloxanes alone.

It was, therefore, completely surprising that it is possible to catalyze the equilibration of organosiloxanes containing no condensable groups in a manner such that no oligomeric cyclic organosiloxanes are formed. It was surprising, furthermore, that compounds were found which catalyze exclusively the equilibration and not the formation of cyclic components.

The polyorganosiloxanes obtained using the novel process feature great uniformity in terms of molecular weight distribution and statistical distribution of the functional groups. If, for example, two α,ω-bis(trimethylsiloxy) polydimethylsiloxanes which differ sufficiently in their viscosity are mixed with one another, it is possible by GPC (gel permeation chromatography) of this mixture to measure a ratio of weight-average to number-average molecular weight (dispersity or molecular weight distribution MWD) which is greater than that of the starting components. The decrease in dispersity over time which is observed following the addition of the catalyst shows that an equilibration reaction takes place. The result of this is a molecular weight distribution as is also achieved by conventional polymerization/ equilibration reactions. In contrast to the known prior art, however, this equilibration takes place without the formation of notable concentrations of cyclic siloxanes.

A preferred variant of the novel process is the preparation of polyorganosivloxanes having statistically distributed lateral silicon-bonded hydrogen atoms from trialkylsiloxy-terminated polyorganosiloxanes and the nonvolatile fraction of the hydrolyzate of triorganochlorosilanes and organodichlorosilanes. Such polyorganosiloxanes are used, for example, as crosslinkers for addition-crosslinking silicone rubber or as starting material for the preparation of specific organomodified polyorganosiloxanes.

Organofunctionally modified polysiloxanes of the general formula

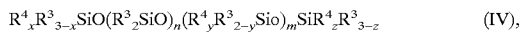          (IV), in which $R^3$ denotes identical and/or different, substituted and/or unsubstituted, saturated and/or unsaturated monovalent hydrocarbon radicals having 1 to 6 carbon atoms, $—(—R^3{}_2SiO—)$, $—(—R^4{}_yR^3{}_{2-y}SiO—)$ and/or $—(—R^4{}_xR^3{}_{3-x}SiO)$ groups, and $R^4$ denotes identical and/or different, substituted and/or unsubstituted, saturated and/or unsaturated, branched and/or unbranched hydrocarbons and/or organic polymers having 1 to 500 carbon atoms or R, n adopts values from 1 to 5000 and m adopts values from 1 to 1000, and x, y and z are either 0 or 1, with the proviso that at least one of the parameters x, y or z adopts the value 1, are obtained by reacting (a) polyorganosiloxanes comprising substantially no cyclic components, prepared in a preceding stage as described, which comprise at least one silicon-bonded hydrogen, with (b) one or more unsaturated, substituted and/or unsubstituted, branched and/or unbranched hydrocarbons and/or organic polymers having 1 to 500 carbon atoms, which are accessible to hydrosilylation reactions, in the presence (c) of a customary hydrosilylation catalyst.

The compounds of the general formulae (I), (II) and (III) should contain—as unsaturated hydrocarbon radicals R, $R^1$ and $R^2$—only those unsaturated groups which are of little or no accessibility to the hydrosilylation reaction in the presence of the particular hydrosilylation catalysts employed or which do not hinder or suppress this reaction by deactivating the catalyst, for example by complexing or poisoning. Those permissible are in almost all cases aryl radicals, such as phenyl, naphthyl or anthryl groups, alkylaryl radicals, such as tolyl, ethylphenyl or mesityl groups, and unsaturated hydrocarbon groups in which the double or triple bond can be hydrosilylated not at all or only very little by steric, inductive or mesomeric effects. This relates, for example, to 1-phenylcyclohexenyl groups having sterically bulky groups, such as tertiary butyl or isopropyl fragments, substituted vinyl or allyl radicals, and also, for example, to vinylamine or allylamine double bonds that are delocalized by means of electron donors, for example.

The polyorganosiloxanes employed (general formula (I)) in this case correspond preferably to the general formula

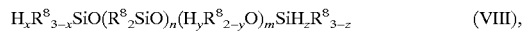          (VIII), in which $R^8$ is identical or different and is alternatively $R^3{}_1—(—H_yR^3{}_{2-y}SiO—)$ and/or $—(—H_xR^3{}_{3-x}SiO—)$ groups and $R^3$, n, m, x, y and z possess the meaning indicated in the general formula (IV).

The polyorganosiloxanes of the general formula (VIII) are preferably prepared by reacting one or more hydrido-functional polyorganosiloxanes of the general formula

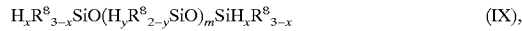          (IX), in which $R^8$, m, x and y possess the meaning indicated above, with one or more polyorganosiloxanes of the general formula

          (X), in which R and n possess the meaning given above, in the presence of a catalyst, with the proviso that no amounts or only very small amounts of cyclosiloxanes are formed.

Examples of the radicals $R^8$ are n-alkyl radicals having 1 to 20 carbon atoms such as, for example, methyl, ethyl, hexyl and cyclohexyl; isoalkyl radicals having 3 to 20 carbon atoms, such as isopropyl and isoamyl radicals; alkyl radicals having tertiary carbon atoms, such as tert-butyl and tert-pentyl; aromatic hydrocarbon radicals, for example: phenyl, naphthyl and anthryl radicals; alkylaryl radicals in which the silicon is attached either to an aromatic carbon atom, as, for example, in the case of tolyl radicals, or to an aliphatic carbon atom, as, for example, in the case of benzyl radicals; and also substituted hydrocarbon radicals, for example trifluoropropyl, cyanoethyl, alkoxyaryl, alkoxy-alkyl and haloaryl radicals. Particularly referred radicals $R^8$ are methyl, phenyl and hydrogen radicals.

Examples of compounds of the general formula (VIII) are polydimethylsiloxanes with trimethylsiloxy end groups, polydimethylsiloxanes with dimethylhydridosiloxy end groups, polymethylhydridosiloxanes with trimethylsiloxy end groups and/or dimethylhydridosiloxy end groups, and polydiorganosiloxanes with lateral and/or terminal saturated hydrocarbon groups.

As polymers and/or hydrocarbons mentioned under (b) use is preferably made of compounds containing at least one olefinic double bond and/or triple bond and/or which belong to the group of the carbonyl compounds, carbonyl analogs and/or heteroanalog carbonyl compounds. For example, the hydrocarbons contain at least one vinyl and/or allyl group and are selected from the group of the unsaturated hydrocarbons and/or of the halo-, epoxy-, ether-, alkoxy-, carboxy-, acrylic-, aryloxy-, methacrylic-, methacryloyloxyand/or nitrogen-functional hydrocarbons. Thus it is possible for the hydrocarbons specified under (b) to be terminal aliphatic and/or aromatic olefins having 3 to 40, preferably 8 to 25, carbon atoms, unsaturated fatty acids or derivatives thereof, it is of course also possible to employ unsaturated organosilicon compounds, for example methacryloylpropyltrialkylsilanes or -siloxanes as compound (b).

Furthermore, the polymers and/or hydrocarbons mentioned under (b) can be allylated polyethers of the general formula

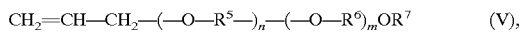
$$CH_2=CH-CH_2-(-O-R^5-)_n-(-O-R^6)_m OR^7 \qquad (V),$$

in which $R^5$ and $R^6$ independently of one another denote branched and/or unbranched hydrocarbons having 1 to 6 carbon atoms and $R^7$ is alternatively $R^5$, $R^6$ or hydrogen and n and m adopt the values indicated above.

As hydrosilylation catalyst use is made of metals and/or compounds of the metals of the 8th subgroup of the Periodic Table of the Elements, for example hexachloroplatinic acid, dissolved in alcohols, preferably in isopropanol (Speier catalyst) or in ethanol (Lamoreaux catalyst) or in protic, apolar hydrocarbons, such as toluene, benzene, hexane or xylene, vinylsiloxane-platinum complexes (Karstedt catalysts) or rhodium complexes, such as rhodium-chlorotriphenylphosphine complexes (Wilkinson catalysts). It is also possible to use the platinum catalyst fixed on a support, for example in colloidal form on active charcoal. Independently of this, however, it is also possible to employ compounds of the metals Pd, Co, Ni, Ru, Cu, Ir, Fe, Mo, W, Os, Cr, Zr and Ti as hydrosilylation catalysts, it is likewise possible to include known inhibitors, for example dialkyl maleate or alkynols, to control the reaction rate. The amount of catalyst used is from 0.1 to 100 ppm, preferably from 5 to 50 ppm, based on the sum of the amounts of (a) and (b).

The reaction of the polyorganosiloxanes (a) with the hydrocarbons and/or organic polymers (b) in the presence of the hydrosilylation catalyst (c) is effected by mixing (a) and (b) and adding the catalyst. The sequence of the addition is not critical in the majority of cases. Where the compounds (a) and (b) are not miscible with one another or if the viscosity of the mixture is too high, it is sensible to employ a solvent and/or a solubilizer. To this end the unsaturated hydrocarbon described under (b) in the main claim is customarily introduced in a solution of an aprotic solvent, such as saturated hydrocarbons, benzene, toluene or xylene, and the hydrido-functional polyorganosiloxane of the general formula (II) and the respective catalyst are added. These additives must not of course adversely affect the course of the reaction—compounds which have proved to be suitable for this purpose are aromatic hydrocarbons, such as toluene in particular.

The proportion of (a) to (b) is dependent on the desired product of the general formula (IV). Preferably, and in order to rule out unwanted side reactions, an approximately equimolar proportion of silicon-bonded hydrogen atoms to saturated groups is chosen. However, it is possible for (a) or (b) to be present in excess.

The temperatures during the reaction are up to 200° C., with temperatures from 20 to 150° C., for example from 50 to 120° C., being preferred. The reaction leads after about 1 min to 20 h to a degree of reaction of more than 95%, which can easily be determined by the amount of hydrogen which can still be eliminated by the action of bases from remaining H—Si groups.

The organofunctionally modified polysiloxanes prepared in accordance with the invention have manifold uses. Where the organofunctionally modified polysiloxanes have, for example, amino groups, they can be employed for impregnating textiles. For this purpose emulsions or microemulsions are prepared, preferably with quaternization of the amine nitrogen with organic acids, for example acetic acid, and using additional surfactants, and these emulsions or microemulsions, following dilution and, possibly, the addition of further components (catalyst, crosslinker) can be used as an impregnating bath. Application in the form of a solution is likewise possible.

Polysiloxanes prepared in accordance with the invention which carry long alkyl, alkylaryl and/or polyether groups may be used as release agents, antifoams or emulsifiers. Workpieces which come into contact with such polysiloxanes can be subsequently coated or bonded without exhibiting the typical silicone defects, for example "fish eyes".

Polysiloxanes substituted by long alkyl or long alkylaryl radicals can be employed, for example, as emulsifiers where mineral oils are to be emulsified in silicone oils. If the polysiloxanes prepared in accordance with the invention carry polyether groups, they are outstandingly suitable as emulsifiers for aqueous media, for example for the preparation of antifoam dispersions.

A particularly preferred field of use of polyether-modified polysiloxanes is their use for stabilizing polymer foams. For this purpose use may be made, for example, of polysiloxanes of the general formula

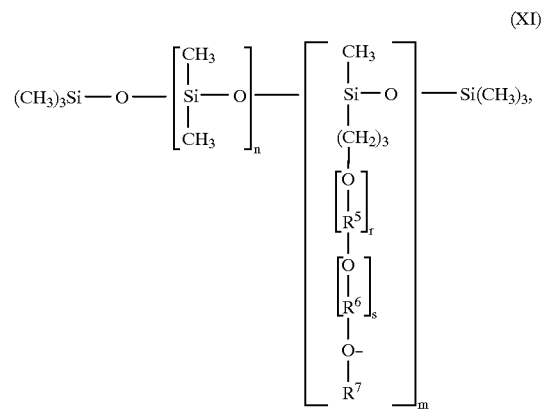

(XI)

in which $R^5$, $R^6$, $R^7$, n and m are as defined above and r adopts the values of n and s adopts the values of m. These compounds are highly effective stabilizers for polyurethane foams. On the basis of the sensitive rigid and flexible PU foam systems, the increased effectiveness of the polyether-modified polysiloxanes prepared in accordance with the invention relative to the prior art is demonstrated outstandingly. For this use the polyol component is reacted with a di- and/or polyfunctional isocyanate compound in the presence of catalysts and blowing agents and also, if desired, of customary antioxidants and flame retardants. Blowing agents which may be used are water, volatile organic compounds, such as pentanes or else fluorocarbons, or mixtures thereof. Examples of the polyol components are alkylene oxide adducts of polyfunctional alcohols, of non-reducing carbohydrates (e.g. nonreducing sugars) or of derivatives thereof, such as glycosides, or of polyfunctional phenols. In addition, however, polyfunctional alcohols of low molecular mass, such as glycerol or ethylene glycol, can be used. Through the use of mixtures of various polyols it is possible to finetune the physical properties.

WORKING EXAMPLES

All viscosity data relate to 25° C.
Preparing the catalysts

Phosphonitrile chloride A

The phosphonitrile chloride A (PN-A) employed as starting product was prepared in accordance with U.S. Pat. No. 3,839,388 as follows:

99.1 g of 1,2,3-trichloropropane, 3.8 g of ammonium chloride and 32.8 g of phosphorus pentachloride were mixed at room temperature by intensive stirring for 30 minutes in a 1.5 l sulfonating flask equipped with stirrer, baffle insert, thermometer, dropping funnel and intensive condenser. With uninterrupted stirring the reaction mixture was heated first at 130° C. for 6 h and then at 150° C. for a further 6 h. The 13.7 g of hydrogen chloride formed in the reaction were absorbed in a downstream water-filled wash bottle. After the reaction had ended and the reaction mixture had been cooled to room temperature, the solvent was distilled off at a pressure of 5 mbar up to a bottom temperature of 130° C. The 20 g of phosphonitrile chloride obtained corresponded to the general formula $[Cl_3P=N(-PCl_2=N-)_xPCl_3]^+[P_yCl_{5y+1}]^-$ in which x is an integer greater than or equal to 0 and y is 0 or 1. For subsequent reaction dilution was carried out with an arbitrary diluent, for example with methylene chloride.

Phosphonitrile chloride B

The phosphonitrile chloride B (PN-B) employed as starting product was prepared in accordance with DE 42 21 854 as follows:

200 g of phosphorus pentachloride and 25 g of ammonium chloride were refluxed in 1 l of phosphorus oxychloride for 30 h in the absence of moisture. Subsequently, the residue precipitated at ambient temperature was separated off and the clear solution was concentrated in vacuo to give a yellow, waxlike mass.

Catalysts I and II 5.6 g portions of PN-A or PN-B, respectively, were mixed with 3.53 g of tris(trimethylsilyl) phosphate and the mixture was stirred at a temperature of 60° C. for 0.5 h. The reaction products were mixed with in each case 1110.9 g of a mixture of cyclic polydimethylsiloxanes containing octamethylcyclotetrasiloxane as principal component. The products obtained, referred to below as catalyst I (prepared from PN-A) and catalyst II (prepared from PN-B), are ready-to-use catalysts, the concentration of the reacted phosphonitrile chloride being 0.5% by weight.

Preparing the compounds of the general formula (I)

EXAMPLE 1

Figure 2:
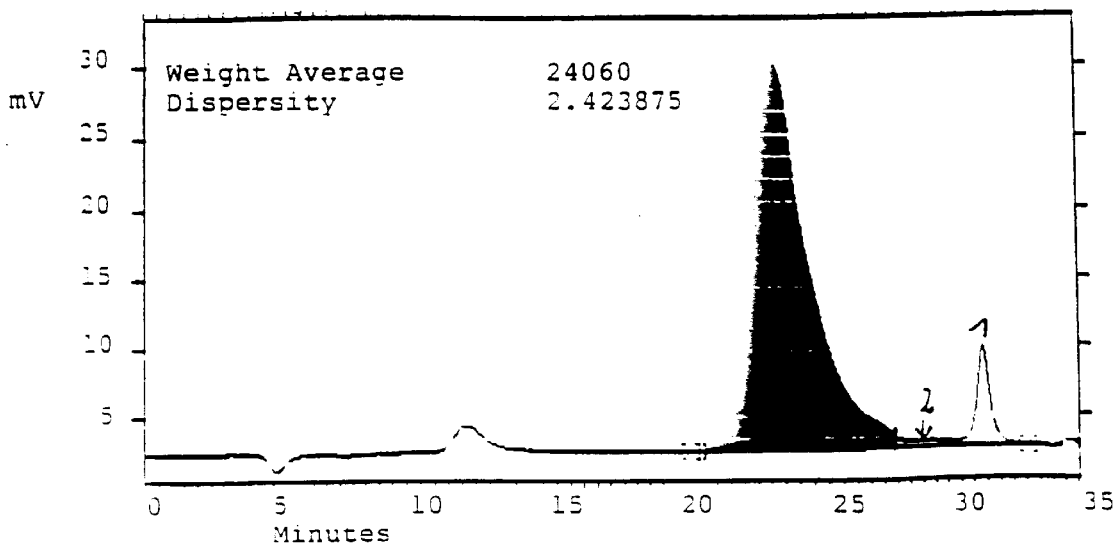

100 g each of a polydimethylsiloxane having trimethylsilyoxy end groups and a viscosity of 100 mPas and of a polydimethylsiloxane having trimethylsiloxy end groups and a viscosity of 100,000 mPas were mixed with one another and heated to 100° C. Following the addition of 0.8 g of a 0.25% strength by weight solution of PN-A in methylene chloride, GPC was used to investigate the decrease in dispersity (MWD) and the content of cyclic siloxanes. Over the course of 10 minutes the dispersity of the siloxane mixture fell from 8.9 (FIG. 1; 1—standard peak in n-hexane, 2—elution time for cyclic compounds peak) to 2.6 and after 30 minutes remained constant at a level of 2.4 (FIG. 2; 1 and 2, see FIG. 1). The reaction product was neutralized by mixing it with 4 mg of triisooctylamine. The content of cyclosiloxanes (elution time 28/29 min) was 0.5% by weight in the initial mixture and, in the reaction product after 30 minutes, 0.9% by weight, and had thus shown no notable increase.

EXAMPLE 2

100 g of a mixture of 99.5 g of a polydimethylsiloxane having trimethylsilyoxy end groups and a viscosity of 85,000 mPas and 0.5 g of hexamethyldisiloxane were heated to 80° C., and 0.4 g of 0.25% strength by weight solution of PN-B in phosphorus oxychloride was added. The viscosity of the initial mixture was 53,500 mPas and the content of cyclic siloxanes was 0.6% by weight. After 100 minutes measurements carried out on the reaction product, which was neutralized by being mixed with 2 mg of triisooctylamine, gave a viscosity of 21,000 mPas and a content of cyclic siloxanes of 0.7% by weight.

EXAMPLE 3

100 g of a mixture of 99.5 g of a polydimethylsiloxane having dimethylvinylsiloxy end groups and a viscosity of 110,000 mPas and 0.5 g of tetramethyldivinyidisiloxane were heated to 80° C., and 0.4 g of the catalyst II was added. The viscosity of the initial mixture was 86,500 mPas and the content of cyclic siloxanes was 0.8% by weight. After 50 minutes, measurement of the reaction product, which was neutralized by being mixed with 2 mg of triisooctylamine, gave a viscosity of 15,100 mPas and a content of cyclic siloxanes of 0.9% by weight.

EXAMPLE 4

100 g of a mixture of 95 g of a polydimethylsiloxane having dimethylvinylsiloxy end groups and a viscosity of 110,000 mPas and 5 g of a polydimethylsiloxane having dimethylvinylsiloxy end groups and containing 10% by weight of dimethylvinylsiloxy groups were heated to 80° C., and 0.4 g of a 0.25% strength by weight solution of PN-A in methylene chloride was added. The viscosity of the initial mixture was 84,500 mPas and the content of cyclic siloxanes was 0.9% by weight. After 75 minutes, measurement of the reaction product, which was neutralized by being mixed with 2 mg of triisooctylamine, gave a viscosity of 14,000 mPas and a content of cyclic siloxanes of 1.1% by weight.

EXAMPLE 5

137.5 g/h of a polymethylhydrosiloxane having trimethylsiloxy end groups and a viscosity of 32 mPas, 162.5 g/h of a polydimethylsiloxane having trimethylsiloxy end groups and a viscosity of 50 mPas and 1.2 g/h of the catalyst I were mixed with one another continuously in a static mixer which is kept at a temperature of 100° C. After a residence time of 30 minutes, the catalyst was deactivated with 1.2 g/h of a 1% strength solution of triisooctylamine in a polydimethylsiloxane having trimethylsiloxy end groups and a viscosity of 50 mPas, in a downstream static mixer. The product obtained was a terminally trimethylsiloxy-blocked polyorganosiloxane which contained both dimethyl- and methylhydrosiloxy groups. The viscosity of the polyorganosiloxane was 47 mPas and its content of cyclic siloxanes was 1.2% by weight.

EXAMPLE 6

600 parts of a polydimethylsiloxane having dimethylvinylsiloxy end groups and a viscosity of 10,000 mm$^2$/s and 200 parts of a polydimethylsiloxane having trimethylsiloxy end groups and a viscosity of 350 mm$^2$/s were mixed, 20 ppm of trifluoromethanesulfonic acid were added, the mixture was heated at 70° C. for 2 h, and then the catalyst was neutralized with 50 ppm of trisisooctylamine. GPC showed a nonuniform molecular weight distribution (MWD=$M_w$/$M_n$=3.9) before the reaction and a uniform molecular weight distribution (MWD=3.1) after the reaction. Surprisingly, no increase in oligomeric cyclic siloxanes was found.

EXAMPLE 6 A (Application Example)

272 parts of hydrophilic pyrogenic silica with a BET surface area of 200 g/m$^2$ and 1728 parts of a polydimethylsiloxane with a viscosity of 200 mm$^2$/s were stirred together intimately and milled 3 times using a colloid mill. The mixture was subsequently heated at 130° C. for 5 h and milled again with the colloid mill. 600 parts of this silica dispersion, 200 parts of the polyorganosiloxane prepared in accordance with Example 6, 2 parts of a siloxane of the formula $(CH_3)_3SiO[Si(CH_3)(H)O]_4[Si(CH_3)_2O]_8Si(CH_3)_3$ and 0.3 part of 0.1 molar hexachloroplatinic acid in isopropanol (Speier catalyst) were mixed and the mixture was heated at 70° C. for 1 hour, during which the silicon-bonded hydrogen atoms reacted with the unsaturated hydrocarbon radicals. Although stoichiometric amounts of the siloxane with silicon-bonded hydrogen atoms and of the siloxane with unsaturated hydrocarbon radicals were used, there was no excessive increase in viscosity or even gelling of the product. This demonstrates the statistical distribution of the dimethylvinyl end groups. The product could be employed as an antifoam with outstanding effectiveness.

EXAMPLE 6 C (Comparison Example)

The experiment was conducted analogously to Example 6 but the catalyst used, in a manner not in accordance with the invention, was 50 g of an acidic ion exchanger. After only 8 h at 80° C. 11% by weight of oligomeric cyclic siloxanes had formed and the molecular weight distribution was very broad and nonuniform (MWD=3.6). This product could not be processed further.

EXAMPLES 7 to 9

The procedure was analogous to Example 6, but the catalyst used was 25 ppm of trifluoromethanesulfochloride (Example 7), 50 ppm of nonafluorobutylsulfonic acid (Example 8) and 20 ppm of trifluoromethanesulfonic anhydride (Example 9), respectively.

In each case a polymer with uniform molecular weight distribution but without a disruptive, increased content of cyclic compounds was obtained.

EXAMPLE 11

20 ppm of trifluoromethanesulfonic acid were added to a mixture of 25 parts of the nonvolatile fraction of the hydrolysate of trimethylchlorosilane and methyidichlorosilane (average formula $Me_3SiO[Si(Me)(H)O]_{50}SiMe_3$, Me=methyl) and 450 parts of a polydimethylsiloxane having trimethylsiloxy end groups and a viscosity of 50 mm$^2$/s, and the mixture was stirred at 80° C. for 8 h. The catalyst was deactivated by adding 50 ppm of trisisooctylamine. $^{29}$Si-NMR showed that the Si—H groups were distributed statistically over the polymer chain.

In the GPC diagram for this mixture, no peak was found in the region of the cyclic siloxanes.

EXAMPLE 12

Preparing a polyether-polysiloxane block copolymer and testing it as stabilizer for PU foam.
Stage 1
Preparing the polyorganosiloxane of the general formula (I)
In a 1 l three-necked flask with stirrer, N$_2$ blanketing, thermometer and adjustable heating, 450 g of a trimethyl-siloxy-terminated polydimethylsiloxane having a viscosity of 50 mPas and 63 g of a polysiloxane containing silicon-bonded hydrogen of the average formula $(CH_3)_3SiO[Si(CH_3)(H)O]_{45.3}Si(CH_3)_3$ (1 i) were intimately mixed over the course of 15 minutes and heated to 65° C. Following the injection of 0.5 g of a polydimethylsiloxane containing 2% by weight of phosphonitrile chloride, the reaction was carried out at 65° C. and was terminated after 1.5 h by injecting 0.15 ml of a 10% strength solution of triisooctylamine in a polysiloxane containing silicon-bonded hydrogen. Analysis gave a viscosity of 42 mPas, a content of cyclic compounds of 1.5% by weight and a hydrogen content of 0.192% by weight (H—Si). On the basis of $^{29}$Si-NMR spectroscopy the polyorganosiloxane obtained was found to have an average formula of $(CH_3)_3SiO[Si(CH_3)(H)O]_{7.2}[Si(CH_3)_2O]_{43}Si(CH_3)_3$ (1j) and the statistical distribution of the methylhydridosiloxy groups in the polymer was demonstrated.
Stage 2
Preparing the polysiloxane of the general formula (IV)

250 ml of toluene and 195 g of a dried allyl polyether of the average formula $CH_2=CH-CH_2-(O-CH_2-CH_2)_{18}-(O-CH_2-CH(CH_3))_{12}-O-(CH_2)_3CH_3$ (1k) were charged to a 1 l three-necked flask with stirrer, N$_2$ blanketing, thermometer, heating and reflux condenser, the mixture was heated to 90° C. and blanketed with N$_2$, and 58 g of the polyorganosiloxane synthesized in stage 1 and 6 ppm of platinum in the form of a 0.01 molar solution of H$_2$PtCl$_6$ in isopropanol were added rapidly. The exothermic reaction led to a temperature increase by 10° C. and the turbid mixture clarified after 60 seconds. To complete the reaction, the reaction was continued at 105° C. for 1 h more and then the toluene was distilled off in vacuo. The polyether-modified polysiloxane, which corresponded to the general formula (XI) with $R^5$=—CH$_2$—CH$_2$—; $R^6$=—CH$_2$—CH(CH$_3$)—; $R^7$=—(CH$_2$)$_3$CH$_3$ and n=43, m=7.2, r=18 and s=12, was obtained as a liquid which was clear and only in thick layer showed a pale yellow color, with a viscosity of 760 mPas. Analysis for H—Si groups indicated a degree of conversion of 98.5%.

EXAMPLE 12 C (Comparison Example)

In accordance with the prior art, the polyorganosiloxane of the average formula (1j) was prepared by equilibrating for 20 hours a mixture of 842.6 g of polydimethylcyclosiloxanes, 121.2 g of the hydrido-functional polysiloxane of formula (1i) and 36.2 g of hexamethyidisiloxane in the presence of 3% by weight of a customary commercial acidic (sulfonic acid) ion exchanger. After removal of the catalyst used by filtration, the resulting hydrido-functional polyorganosiloxane (hydrogen content: 0.191% by weight (H—Si); viscosity: 38 mPas, content of cyclic compounds: 12% by weight) was distilled in vacuo and employed for the next stage. The addition reaction of the allyl polyether of the formula (1k), carried out in accordance with Example 1, stage 2, led to product 1a (degree of conversion: 98%; viscosity: 910 mPas).
Testing of the polysiloxanes as foam stabilizers The polyether-modified polysiloxanes prepared in accordance with Examples 12 and 12 C were tested for their effectiveness in respect of height of rise and porosity in a commercial, 141b(HFC)-blown rigid foam system and in respect of height of rise and air permeability in a commercial CO$_2$-blown flexible foam system.

The results are set out in Table 1.

TABLE 1

| | novel product of Example 12 | non-novel product of Example 12 C |
|---|---|---|
| Rigid foam system | | |
| Parts of polyether-modified polysiloxane per 100 parts of polyol | 1.5 | 1.5 |
| Foaming temperature (° C.) | 40 | 40 |
| Flow length of the foam structure (cm) (lance test) | 158 | 156 |
| Porosity | fine-pored, uniform shape | fine-pored, relatively non-uniform shape |
| Flexible foam test | | |
| Density of the system (kg/m$^3$) | 30 | 30 |
| Parts of polyether-modified polysiloxane per 100 parts of polyol | 0.3 | 0.3 |
| Relative height [1] (%) | 101 | 99 |
| Relative air permeability [1] (%) | 100 | 90 |

[1] relative to 0.9 part of a comparison stabilizer of recognized quality

The polyether-modified polysiloxane of Example 12, prepared in accordance with the invention, with an analogous basic structure, showed advantages relative to the non-novel product 12 C prepared from distilled H-polysiloxane both in the rigid foam system used and in the commercial flexible foam system.

EXAMPLES 13 to 16

Preparing polysiloxanes modified in different ways

The polysiloxane used was the hydrido-functional polysiloxane (1j) prepared in accordance with Example 1.

Using various unsaturated functional hydrocarbons, organomodified polysiloxanes were prepared in accordance with Table 2 in the presence of various customary hydrosilylation catalysts. The reactions proceeded with good yields and gave products which were clear to pale yellow in color.

TABLE 2

| Ex. No. | Hydrocarbon [g] | Catalyst [ppm] | Siloxane (7j) [g] | Reaction time [h] | Reaction temp. [° C.] | Product visc. [mPas] | Degree of conversion [%] |
|---|---|---|---|---|---|---|---|
| 13 | CH$_2$=CH—CH$_2$—NO$_2$ [20] | H$_2$PtCl$_6$ [50] | 100 | 6 | 80 | 61 | 92 |
| 14 | CH$_2$=CH—OCOCH$_3$ [20] | H$_2$PtCl$_6$ [50] | 100 | 10 | 90 | 71 | 90 |
| 15 | (CH$_3$)$_2$—C=CHCOCH$_3$ [20] | Rh(P—Ph$_3$)Cl [200] | 100 | 10 | 80 | 74 | 98 |
| 16 | 2-propargyl-oxyethyl acrylate [35] | PtCl$_4$(1-octene) [50] | 100 | 3 | 110 | 81 | 97 |

What is claimed is:

1. A process for preparing polyorganosiloxanes which comprise substantially no cyclic components and have a uniform molecular weight distribution, which comprises reacting two or more organosiloxanes and/or polyorganosiloxanes of the general formula $$R_aSiO_{(4-a)/2} \quad (I)$$

which comprise at least one siloxy group of the general formula $$R_3SiO_{0.5-} \quad (M),$$

and at least one siloxy group of the general formula $$R_2SiO— \quad (D),$$

where R denotes identical or different, saturated and/or unsaturated, substituted and/or unsubstituted, monovalent hydrocarbon radicals having 1 to 30 carbon atoms or hydrogen, with the proviso that only one hydrogen is attached per silicon, and a is an integral or fractional numbers greater than 1, said polyorganosiloxanes of the general formula (I) comprising substantially no condensable groups, are reacted in the present of a catalyst which exclusively promotes equilibration and suppresses formation of cyclic components, wherein said catalyst comprises a reaction product of phosphonitrile chloride with compounds of the general formula $$[R^1{}_3SiO(R^1{}_2SiO)_n]_3P=O \quad (II)$$

in which $R^1$ independently of each other denotes identical or different, substituted and/or unsubstituted, unsaturated and/or saturated monovalent hydrocarbon radicals having 1 to 6 carbon atoms or hydrogen, with the proviso that only one hydrogen atom is attached to each silicon atom, and n has a value of between 0 and 500.

2. The process as claimed in claim 1, wherein the catalyst is employed in amounts of from 0.1 to 100 ppm by weight, based on the overall weight of the starting materials.

3. The process as claimed in claim 2, wherein the catalyst is employed in amounts of from 5 to 20 ppm by weight, based on the overall weight of the starting materials.

4. The process as claimed in claim 1, wherein following the reaction the catalyst is deactivated and/or separated off.

5. The process as claimed in claim 1, wherein a in the general formula (I) has a value of from 1.8 to 2.2.

6. The process as claimed in claim 1, wherein no water or organic solvents are added.

7. A hydrosilylation process for preparing substantially noncyclic, organofimctionally modified polysiloxanes of the general formula

  (I)

in which $R^3$ denotes identical and/or different, substituted and/or unsubstituted, saturated and/or unsaturated monovalent hydrocarbon radicals having 1 to 6 carbon atoms, $—(—R^3{}_2SiO—)$, $—(—R^4{}_yR^3{}_{2-y}SiO—)$ and/or $—(—R^4{}_xR^3{}_{3-x}SiO)$ groups, and $R^4$ denotes identical and/or different, substituted and/or unsubstituted, saturated and/or unsaturated, branched and/or unbranched hydrocarbons and/or organic polymers having 1 to 500 carbon atoms or R, n has values from 1 to 5000 and m has values from 1 to 1000, and x, y and z are either 0 or 1, with the proviso that at least one of x, y or z has a value of 1, comprising reacting (a) polyorganosiloxanes prepared as claimed in claim 1 which comprise at least one silicon-bonded hydrogen, with (b) one or more unsaturated, substituted and/or unsubstituted, branched and/or unbranched hydrocarbons and/or organic polymers having 1 to 500 carbon atoms, which are accessible to hydrosilylation reactions, in the presence (c) of a hydrosilylation catalyst.

8. The process as set forth in claim 7, wherein the polymers and/or hydrocarbons of (b) contain at least one olefinic double bond and/or triple bond and/or are carbonyl compounds.

9. The process as claimed in claim 8, wherein the polymers and/or hydrocarbons of (b) contain at least one vinyl and/or allyl group and are selected from the group consisting of unsaturated hydrocarbons, halo-, epoxy-, ether-, alkoxy-, carboxy-, acrylic-, aryloxy-, methacrylic-, methacryloyloxy, nitrogen-functional hydrocarbons and mixtures thereof.

10. The process as claimed in claim 8, wherein the polymers and/or hydrocarbons of (b) are allylated polyethers of the general formula

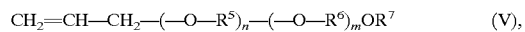  (V), in which $R^5$ and $R^6$ independently of one another denote branched and/or unbranched hydrocarbons having 1 to 6 carbon atoms and $R^7$ is alternatively $R^5$, $R^6$ or hydrogen, n has a value of 1 to 5000 and m has a value of 1 to 1000.

11. The process as set forth in claim 7, wherein the hydrosilylation catalyst comprises metals and/or compounds of metals from the $8^{th}$ subgroup of the Periodic Table of the Elements.

12. The process as claimed in claim 11, wherein the hydrosilylation catalyst comprises hexachloroplatinic acid dissolved in an alcohol.

13. The process as claimed in claim 11, wherein the hydrosilylation catalyst comprises vinylsiloxane-platinum complexes.

14. The process as claimed in claim 11, wherein the hydrosilylation catalyst comprises rhodium complexes.

15. The process as claimed in claim 12, wherein the alcohol is isopropanol.

\* \* \* \* \*